United States Patent
Menzel et al.

(10) Patent No.: US 10,179,838 B2
(45) Date of Patent: Jan. 15, 2019

(54) LOW-SALT PROCESS FOR THE PREPARATION OF A POLYSULFIDE

(71) Applicant: Akzo Nobel Chemicals International B.V., Arnhem (NL)

(72) Inventors: Manfred Menzel, Greiz (DE); Volker Burkhardt, Mörfelden-Walldorf (DE); Olaf Klobes, Greiz (DE)

(73) Assignee: AKZO NOBEL CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 15/534,399

(22) PCT Filed: Dec. 16, 2015

(86) PCT No.: PCT/EP2015/080038
§ 371 (c)(1),
(2) Date: Jun. 8, 2017

(87) PCT Pub. No.: WO2016/097010
PCT Pub. Date: Jun. 23, 2016

(65) Prior Publication Data
US 2018/0265639 A1  Sep. 20, 2018

(30) Foreign Application Priority Data
Dec. 17, 2014  (EP) .................................... 14198572

(51) Int. Cl.
| | | |
|---|---|---|
| *C08G 75/14* | (2006.01) | |
| *C08G 75/16* | (2006.01) | |
| *C07C 43/315* | (2006.01) | |
| *C08L 81/04* | (2006.01) | |

(52) U.S. Cl.
CPC ............ *C08G 75/16* (2013.01); *C07C 43/315* (2013.01); *C08L 81/04* (2013.01)

(58) Field of Classification Search
CPC .......... C08L 61/04; C08L 61/06; C08L 81/02; C08L 81/04; C07C 323/12; C07C 43/315; C08G 65/34; C08G 65/38; C08G 75/10; C08G 75/12; C08G 75/14; C08G 75/16; C08G 75/045
See application file for complete search history.

(56) References Cited

U.S. PATENT DOCUMENTS

| | | | |
|---|---|---|---|
| 2,382,874 A | | 8/1945 | Gresham et al. |
| 2,553,206 A | * | 5/1951 | Patrick .................... C08G 75/16 528/265 |
| 2,728,748 A | | 12/1955 | Davis |
| 3,305,536 A | | 2/1967 | Warner |
| 3,647,766 A | | 3/1972 | Bertozzi |
| 4,124,645 A | | 11/1978 | Bertozzi |
| 5,430,192 A | * | 7/1995 | Hobbs .................... C07C 323/12 568/22 |
| 9,631,055 B2 | | 4/2017 | Menzel et al. |
| 2003/0050511 A1 | | 3/2003 | Gilmore et al. |
| 2006/0094831 A1 | | 5/2006 | Choi et al. |
| 2007/0249860 A1 | | 10/2007 | Zeitler et al. |

FOREIGN PATENT DOCUMENTS

| | | |
|---|---|---|
| DE | 35849 | 1/1965 |
| DE | 238967 A1 | 9/1986 |
| DE | 251257 A3 | 11/1987 |
| EP | 0043043 A1 | 1/1982 |
| EP | 0 547 905 A1 | 6/1993 |
| EP | 2 738 160 A1 | 6/2014 |
| JP | 62-019580 A | 4/2006 |
| WO | 2006/037442 A1 | 4/2006 |
| WO | 2007/101819 A1 | 9/2007 |
| WO | 2012/139984 A1 | 10/2012 |

OTHER PUBLICATIONS

European Search Report issued in counterpart EP Application No. 14198572.1 dated May 27, 2015.
International Search Report and Written Opinion for PCT/EP2015/080038 dated Feb. 19, 2016.
Jorczak et al., "Polysulfide Liquid Polymers," Industrial and Engineering Chemistry, vol. 43, No. 2, Feb. 1951, pp. 324-328, XP009107340.
Matsui et al., "Detection of a New Crosslinking and Properties of Liquid Polysulfide Polymer," Journal of Applied Polymer Science, vol. 71, Jan. 1999, pp. 59-66, XP002239279.
Lowe et al., "Water durability of adhesive bonds between glass and polysulfide sealants," Int. J. Adhesion and Adhesives, vol. 14, No. 2, Apr. 1994, pp. 85-92, XP009009894.
Kirk-Othmer, Encyclopedia of Chemical Technology, $3^{rd}$ Ed., vol. 18, Plant-Growth Substances to Potassium Compounds, Polymers Containing Sulfur (Polysulfides), p. 815.
J.R. Panek, XIV. Polysulfide Polymes: II. Applications, Polyethers, Part III, Thiokol Chemical Corp., Trenton, New Jersey, p. 115-215.

\* cited by examiner

*Primary Examiner* — Christopher M Rodd
(74) *Attorney, Agent, or Firm* — Sandra B. Weiss

(57) ABSTRACT

Process for the preparation of a polysulfide comprising the step of reacting in the absence of a dihaloalkane a bis(2-dihaloalkyl)formal in the presence of (i) a pre-polymer (I) according to structure (I)

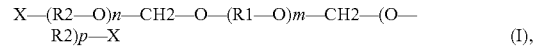

wherein R1 and R2 can be the same or different and are selected from alkane chains containing 2-10 carbon atoms, X is a halogen atom, and n, m, and p are integers that can be the same or different and have a value in the range 1-6, with either (i) sodium polysulfide or (ii) a combination of sodium hydrosulfide and sulfur.

13 Claims, No Drawings

LOW-SALT PROCESS FOR THE PREPARATION OF A POLYSULFIDE

This application is a national stage filing under 35 U.S.C. § 371 of PCT/EP2015/080038, filed Dec. 16, 2015, which claims priority to European Patent Application No. 14198572.1, filed Dec. 17, 2014, the contents of each of which are each incorporated herein by reference in their entirety.

The present invention relates to a process for the preparation of a polysulfide.

Polysulfides are a class of polymers (in the following polysulfides) with alternating chains of several sulfur atoms and hydrocarbons. The general formula for the repeating unit is —[R—$S_x$]$_n$—, wherein x indicates the number of sulfur atoms, n indicates the number of repeating units, and R indicates the organic backbone of the polymer. Cured polysulfide polymers are resistant to ageing and weathering, highly elastic from −40 to +120° C., and they offer an outstanding chemical resistance, especially against oil and fuel. Because of their properties, these materials find use as base polymers for sealants applied to fill the joints in pavement, insulation glass units, and aircraft structures.

Polysulfides are conventionally synthesized by reactions between organic dihalides and alkali metal salts of polysulfide anions. Conventional types of polysulfides include solid and liquid polymers.

WO2012/139984, Jorczak et al., *Industrial and Engineering Chemistry*, vol. 43, 1951, p. 324-328, and EP 0 547 905 A1 disclose synthesizing polysulfide polymers by condensation polymerization reactions between organic dihalides such as dichloroalkanes and alkali metal salts of polysulfide anions.

U.S. 5,430,192 and U.S. 2003/0050511 disclose reacting a dihalo oragnic compound such as 1,6-dichlorohexane and/or a chloroethylformal with sodium polysulfide. Lowe et al., *Int. J. Adhesion and Adhesives*, Vol. 14, 1994, p. 85-92, U.S. 4,124,645, Matsui et al., *Journal of Applied Polymer Science*, vol. 71, 1999, p. 59-66, and EP 2 738 160 A1 disclose reacting bis(2-chloroethylformal) with sodium polysulfide or sodium monosulfide (EP 2 738 160 A1), resulting in a polymer of the formula HS—(CH2—CH2—O—CH2—O—CH2—Sx)—H.

Solid polymers have a molecular weight of about $10^5$ g/mol and are prepared from dihaloalkanes (such as 1,2-dichloroethane), alone or in admixture with a bis(2-chloroalkyl)formal, for example bis(2-chloroethyl)formal, and optionally a branching agent such as 1,2,3-trichloropropane.

Liquid polysulfides have a molecular weight of about $10^2$ to $10^3$ g/mol and are generally prepared from a bis(2-chloroalkyl)formal and optionally small amounts of a branching agent like 1,2,3-trichloropropane. The resulting polysulfide is then split into chains of the required lengths by reduction of the disulfide linkages.

A disadvantage of this process is that it does not allow much control over the polarity of the resulting polysulfide. In other words, when using the bis(2-chloroalkyl)formal, such as a bis-(2-chloroethyl)-formal according to the above processes, the polarity of the prepared polysulfide is fixed as follows. The chlorine atoms in the reactants are replaced by sulfur atoms during the polyconensation. The oxygen in the resulting polymer originates from the bis-(2-chloroethyl)-formal, only. Thus, the limiting factor for the ratio of sulfur to oxygen in the resulting polymer is the amount of oxygen in the bis(2-chloroalkyl)formal molecule (e.g. the bis-(2-chloroethyl)-formal molecule).

The polarity of the polysulfide affects its compatibility with surfaces. Polysulfides are often used as sealants for double glazing and in aircrafts. Hence, good compatibility with relatively polar surfaces like glass and metals such as aluminium or steel is required for these applications. The polarity is improved with the introduction of more oxygen relative to sulfur atoms. In addition, the flexibility and elasticity of the polymer at low temperatures and the compatibility of the polymer with plasticizers is improved with higher oxygen content. On the other hand, the chemical resistance against oil and jet fuel improves with a higher content of sulfur relative to oxygen atoms. For aircraft applications, for instance, this leads to conflicting requirements for the sulfur/oxygen ratio of the polymer.

It would therefore be desirable to provide a process that would allow control over the oxygen and sulfur content of the resulting polymer and the possibility to easily adapt this ratio depending on the particular requirements of the product.

Preparing liquid polymers by splitting the chains of solid polymers derived from either dichloroalkane or a combination of dichloroalkane and bis(2-chloroalkyl)formal would not solve these problems because it would lead to liquid polysulfides having a relatively high sulfur content, a relatively low oxygen content and, thus, a relatively low polarity, without suitable means to adapt these properties.

A further disadvantage of the known processes is the formation of large quantities of salt because of the high chlorine content of the used halides. This salt has to be disposed of which has a negative environmental impact and needs an additional economic expenditure.

It is an object of the present invention to provide a polysulfide polymer with good chemical resistance and compatibility with plasticizers and polar surfaces. It is a further object to provide a process that allows control over the oxygen and sulfur content of the resulting polymer and the possibility to adapt this ratio depending on the particular requirements of the product. It is a further object to provide a polysulfide preparation process with low salt production. It is a further object for the prepared polysulfide to have comparable application properties to the application properties of the conventional polysulfides, such as for example cohesion or adhesion behavior, Shore A behavior, and Tensile test (Elongation) behavior of a sealant containing the polysulfide.

These objects are met by the process of the present inevention. Said process involves the prepration of a polysulfide comprising the step of reacting bis(2-chloroalkyl) formal with either (i) sodium polysulfide or (ii) a combination of sodium hydrosulfide (NaHS) and sulfur (S), said reaction being performed in the absence of a dihaloalkane and in the presence of the pre-polymer according to structure (I) X—($R^2$—O)$_n$—$CH_2$—O—($R^1$—O)$_m$—$CH_2$—(O—$R^2$)$_p$—X (I), wherein $R^1$ and $R^2$ can be the same or different and are selected from alkane chains containing 2-10 carbon atoms, and n, m, and p are integers that can be the same or different and have a value in the range 1-6, preferably 1-4.

The reaction is preferably peformed by heating the raction mixture to a temperature in the range 60 to 100° C, more preferably from 80 to 95° and most preferably from 85 to 90° . The conversion time for reacting the mixture is preferably 1-4 hours, more preferably 1-3 hours, and most preferably 1-2 hours.

It is an advantage of the present process that by-product formation, thus salt formation, is reduced compared to the known processes which has an improved environmental impact as less by-product needs to be disposed of. The reduced amount of salt results from the lower halogen content of the reaction mixture. The present process further allows the adjustment of the polarity of the resulting polysulfide by controlling the sulfur to oxygen content of the resulting polysulfide by way of the pre-polymer (I).

Preferably, X is a halogen atom selected from Cl, Br, and I, more preferably Cl, Preferably, $R^1$ is —$CH_2$—$CH_2$—.

The preferred nature of $R^2$ is —$CH_2$—$CH_2$—, —$CH_2$—$CH_2$—$CH_2$—, or —$CH_2$—$CH_2$—$CH_2$—$CH_2$—.

The dihaloalkane which is to be absent from the process has the formula X—R—Y, wherein X and Y are both halogen atoms that may be the same or different, and R is an alkane chain, such as for example R is —$C_2H_4$—, —$C_3H_6$—, or —$C_6H_{12}$—.

The pre-polymer according to structure (I) is obtainable by reacting a polyol with (para)formaldehyde and a halo-alcohol in the presence of an acid catalyst.

Suitable polyols include monoethylene glycol, diethylene glycol, triethylene glycol, tetraethylene glycol, monopropylene glycol, dipropylene glycol, tripropylene glycol, 1,4-butanediol, and mixtures thereof.

Suitable halo-alcohols include chloroalcohols, bromoalcohols, and iodoalcohols, whereby chloroalcohols are preferred. Examples of suitable chloroalcohols are ethylene chlorohydrin (ECH), propylene chlorohydrins, butylene chlorohydrins, pentylene chlorohydrins, and hexylene chlorohydrins. ECH is the most preferred chloroalcohol.

Suitable acid catalysts are HBr, HCl, $H_2SO_4$, $H_3PO_4$, p-toluene sulfonic acid, sulfonic acid, ferric chloride, and cation exchange resins, such as Amberlyst® 15, 31, 35, 36, 39, 119, 131, Lewatite® K1131, K2431, K 2621, and Nafion® SAC-13.

The amount of acid catalyst is preferably in the range of from 0.1 to 10 wt %, based on the weight of entire reaction mixture.

In this specification, the term "(para)formaldehyde" includes formaldehyde (i.e. $CH_2O$) and the condensation products of formaldehyde having the formula $(CH_2O)_n$ that are conventionally referred to as paraformaldehyde. The value of n in this formula is generally in the range 8-100. In the present invention, the use of paraformaldehyde is preferred over formaldehyde.

In the formation of the pre-polymer, the molar ratio of (para)formaldehyde (calculated as $CH_2O$) to OH-functionalities of the polyol is preferably in the range 0.8:1-1.5:1, more preferably 0.9:1-1.3:1, and even most preferably 0.9:1-1.2:1.

The molar ratio of halo-alcohol to OH-functionalities of the polyol is preferably in the range 0.9:1-1.5:1, more preferably 0.9:1-1.4:1 and most preferably 1:1-1.2:1.

The molar ratio of (para)formaldehyde (calculated as $CH_2O$) to halo-alcohol is preferably in the range 0.8:1-1.5:1, more preferably 0.9:1-1.3:1, and most preferably 0.9:1-1.2:1.

The reaction towards the pre-polymer is preferably performed by heating the reaction mixture to a temperature in the range 45-80° C., more preferably 50-75° C., and most preferably 55-65° C. This heating is preferably conducted for 10 minutes to 2 hours, more preferably 20 minutes to 1.5 hours and most preferably 30-60 minutes.

This heating step is preferably followed by two azeotropic distillation steps in order to remove reaction water and any excess of halo-alcohol, thereby shifting the equilibrium towards the pre-polymer.

Suitable bis(2-dihaloalkyl)formals for use in the process of the present invention are bis(2-chloroalkyl)formals, bis(2-bromoalkyl)formals, and bis(2-iodoalkyl)formals. The most preferred bis(2-haloalkyl)formal is bis(2-chloroethyl)formal: Cl—$C_2H_4$—O—$CH_2$—O—$C_2H_4$—Cl.

Sodium polysulfide has the formula $Na_2S_x$, wherein x is in the range 2-5, preferably in the range 2-3, and most preferably in the range 2.2-2.5. The molar ratio of sodium polysulfide (calculated as $Na_2S_x$), relative to bis(2-dihaloalkyl)formal, is preferably in the range 0.8-1.4, more preferably 0.9-1.3, and most preferably 1.0-1.2. Instead of sodium polysulfide, also a mixture of sodium hydrosulfide (NaHS) and sulfur (S) can be used. Preferably the mixture of NaHS and sulfur is an aqueous solution. This has the additional advantage that a splitting step is generally not required.

The weight ratio bis(2-haloalkyl)formal to pre-polymer (I) to be used in the process according to the present invention is preferably in the range 90:10 to 10:90, more preferably in the range 70:30 to 30:70, even more preferably in the range 40:60 to 60:40, and most preferably in the range 45:55 to 55:45.

Optionally a branching agent can be present in the process of the invention. The branching agent serves to form a three dimensional crosslinked structure after curing of the polysulfide and, consequently, a reinforced hardness with good elastic properties of the cured polymer. The branching agent preferably is a trihalide, more preferably 1,2,3-trichloropropane. The branching agent is preferably present in the mixture in an amount of 0.5 to 2 wt %, relative to the weight of bis(2-dihaloalkyl)formal. The branching agent is preferably not a branching agent selected from the group consisting of di-aldehydes and their corresponding acetals and hemiacetals. This means that the process according to the invention is preferably performed in the absence of a branching agent selected from the group consisting of di-aldehydes and their corresponding acetals and hemiacetals.

In one embodiment, the process of the invention is performed by first preparing a mixture comprising the bis(2-haloalkyl)formal, the pre-polymer, and optionally the branching agent, and adding this mixture to an aqueous solution of sodium polysulfide and alkali metal hydroxide whereby the process is performed in the absence of a dihaloalkane. Optionally, a dispersing agent, such as magnesium hydroxide, and/or a wetting agent (e.g. sodium butylnaphthalenesulfonate) may be present in the solution.

The mixture is preferably added slowly, e.g. dropwise, to the solution. The temperature of the solution is preferably in the range 60 to 100° C., more preferably from 80 to 95° C. and most preferably from 85 to 90° C. This addition is preferably conducted for 20 minutes to 2 hours, more preferably 30 minutes to 1.5 hours and most preferably 30-60 minutes.

In a second embodiment, the process of the invention is performed by first preparing a mixture comprising bis(2-haloalkyl)formal and the pre-polymer (I), and optionally the branching agent, and adding this mixture to an aqueous solution of NaHS and sulfur. This embodiment has the additional advantage of a simple process design. The bis(2-haloalkyl)formal-containing mixture is preferably added slowly, e.g. dropwise, to the NaHS and sulfur solution. The temperature of the NaHS and sulfur solution is preferably in the range 60 to 100° C., more preferably from 80 to 100° C. and most preferably from 90 to 100° C. Preferably, a phase transfer catalyst (PTC), such as a quaternary ammonium compound, is added to the mixture. A PTC according to the invention is a catalyst which facilitates the migration of a reactant from a first phase into a second phase, wherein the reaction occurs in the second phase. The polymer obtained in this embodiment is a liquid polysulfide.

In a further embodiment, the process according to the invention is performed by adding the reactants (such as bis(2-chloroalkyl)formal, pre-polymer (I), (i) sodium polysulfide or (ii) a combination of sodium hydrosulfide and sulfur, PTC, the branching agent, the dispersing agent) to one single reactor, preferably sequentially. This embodiment has the additional advantage of a simple process design.

As a subsequent step, the resulting reaction mixture is preferably treated with a desulfurization agent (e.g. sodium hydroxide and sodium hydrogen sulfide) to eliminate any labile sulfur atoms. This desulfurization step can be conducted at a preferred temperature of 80-110° C., more preferably 85-105° C., and most preferably 90-100° C. The reaction time is preferably 1-4 hours, more preferably 1-3 hours, and most preferably 1-2 hours.

In case of reacting the bis(2-haloalkyl)formal in the presence of the pre-polymer (I) with sodium polysulfide according to the invention, the macromolecules in the resulting polysulfide polymer need to be reduced to the required chain length by reductive splitting of the disulfide bonds to obtain a liquid polysulfide. The most common reduction agents are sodium dithionite ($Na_2S_2O_4$) and a combination of NaSH and $Na_2SO_3$. The amount of reduction agent to be used depends on the desired molecular weight, as commonly known in the art.

The preferred reduction agent in the process according to the invention is sodium dithionite. Reductive splitting using sodium dithionite is preferably performed for 20-40 minutes. The temperature preferably ranges from 80 to 110° C., more preferably from 85 to 105° C. and most preferably from 90 to 100° C. The reaction time is preferably 1-4 hours, more preferably 1-3 hours, and most preferably 1-2 hours.

If desired, the splitted disulfide bonds can then be converted into reactive terminal thiol groups by acidification at pH 4-5. Acetic acid is preferably used as the acidifier. Sulfuric acid, formic acid, and citric acid are also preferred acidifiers.

As a last step, the polysulfide can be washed and dewatered under reduced pressure (preferably from 20 to 500 mbar).

The polysulfide resulting from the process of the present invention has various applications, including the use as binder in sealants, adhesives, and coating compositions, in isocyanate cure, in epoxy-resin cure, and in acrylate resin cure.

EXAMPLES

A. Pre-polymer (I) preparation of a pre-polymer (I) mixture based on triethylenglycole (TEG)

A mixture of 4 moles paraformaldehyde (content: 90,5%, supplier Norkem B.V.), 7,5 moles technical ethylene chlorohydrin (ECH) with an average molecular weight of 83,5 g/mol (supplier: CBW Chemie GmbH Bitterfeld), 1 mol TEG (suuplier: Brenntag GmbH) and 5,4 g hydrochloric acid (37%) was heated in a 1,5 liter flask with stirring to about 60° C. until the paraformaldehyde was dissolved. The nearly clear reaction liquid was transferred to a flask of a distillation apparatus with a packed column and subjected to a two stage distillation.

Stage 1: The flask content was gradually heated to 87° C. within 2,5 hours (h) at reduced pressure of 120 mbar. Stage 1 was finished when the head temperature of the distillation had reached 54° C. The Distillate was a mixture of 41% ECH, 58% water and 1% paraformaldehyde.

Stage 2: The flask content resulting from stage 1 was further heated to 135° C. within 1 hour at reduced pressure of 20 mbar. Stage 2 was finished when the head temperature of the distillation had reached 94° C. The distillate was composed of 73% ECH, 8% water, 1,5% HCl and 17,5% bis-(2-chloroethyl)-formal.

The resulting reaction product of 685 g was a mixture of 25% TEG based pre-polymer (I) according to the present invention, 40% bis-(2-chloroethyl)-formal and 35% homologue impurities derived from the pre-polymer (I) and bis-(2-chloroethyl)-formal.

The mixture had a number average molecular weight $M_n$ of 233,1 g/mol and a chlorine content of 30,4 wt%. The chemical structure of the TEG based pre-polymer (I) was determined by means of GC-MS and NMR-spectroscopy.

Example A2: Preparation of a pre-polymer (I) mixture based on diethylenglycole (DEG)

A mixture of 4 moles paraformaldehyde, 6 moles technical ethylenchlorhydrin, 2 moles diethylene glycol (DEG) and 5,4 g hydrochloric acid (37%) was treated according to Example A1. 580 g reaction mixture consisting of 30% DEG based pre-polymer (I), 25% bis-(2-chloroethyl)- formal and 45% homologue impurities were obtained. The mixture had a number average molecular weight $M_n$ of 297,2 g/mol and a chlorine content of 23,9 wt %.

The chamical structure of the DEG based pre-polymer (I) was determined by means of GC-MS and NMR-spectroscopy.

Example A3: Preparation of bis-(2-chloroethyl)-formal (Comperative Example)

A mixture of 4 moles paraformaldehyde, 10 moles technical ethylenchlorhydrin and 5,4 g hydrochloric acid (37%) was treated according to Example A1 without using a polyol as reaction component. 700 g bis-(2-chloroethyl)-formal and its homogues were obtained with a number average molecular weight $M_n$ of 179 g/mol and a chlorine content of 39,6 wt. %.

The obtained mixture was composed of 80 % bis-(2-chloroethyl)-formal and 20% homogue impurities accordin to GC analysis.

B. Polysulfide (PS) preparation

Example B1: Preparation of a polysulfide using the TEG based pre-polymer (I) (A1)

1 Liter of an aqueous 2,2 mol/l $Na_2S_{x\ solution\ (x=2,4)}$ was mixed under stirring in a 2,5 liter flask with 25,1 g 32 % $MgCl_2$ solution, 12 g 50% NaOH solution and 10 ml 30% sodium butylnaphthalene-sulfonate solution and heated to 88° C. A mixture of 512,8 g (2,2 mol) TEG based prepolymer (I) (A1) and 6,5 g (0,044 mol) trichloropropane (TCP) was added within 1 hour while keepign the temperature between 88 and 92° C. After the dosage the reaction mixture was stirred for 30 min at 88-92° C. to complete the raction. Following 100 ml of a 5 molar aqueous $Na_2S$ solution were added. Thereafter, the mixture was heated and stirred for 2 hours at 100° C.

After the reaction, the formed polysulfide latex was washed several times with warm water (50° C.) to remove any soluble salts generated during the condensation process.

In a further step, the washed polysulfide latex was treated with 34 g 90 % sodiumdithionite (0,18 moles), 48,9 g 50 % NaOH solution (0,62 moles) and 66 g 40% sodiumbisulfite solution (0,25 moles) at 98° C. The reaction mixture was stirred for 30 min at 98° C. to complete the reduction process. Subsequently, the product was washed several times with warm water (50° C.) to remove any soluble salts from the polysulfide latex. Thereafter, the polysulfide latex was acidifed with acetic acid to pH 4-5 to coagulate the polysulfide. The coagulated polysulfide was dewatered under reduced pressure (90° C., 20 mbar). The resulting polysulfide was obtained as a viscous yellow brown liquid. The obtained polysulfide had a number average molecular weight $M_n$ in the range of 1800-2700 g/mol.

TABLE B1

| yield polysulfide (PS) (theory): | 503.6 g | measured: | 478.4 g | (= 95.0 % of theory) |
|---|---|---|---|---|
| Cl-content/batch (theory): | 166.7 g | measured: | 165.4 g | (Amount of Cl in the waste water) |
| Cl-emission/kg PS (theory): | 331.0 g | measured: | 345.7 g | |

The ratio of sulfur to oxygen in the obtained polysulfide was derived from the stoichiometry of the reactants as 1:1,7.

Example B2: Preparation of a polysulfide using the DEG based pre-polymer (I) (A2)

The reaction of Example B1 was carried out with 653,8 g (2,2 mol) DEG based pre-polymer (I) (A2) instead of the TEG based pre-polymer (I) (A1). The resulting polysulfide had a number average molecular weight $M_n$ in the range of 1800-2700 g/mol.

TABLE B2

| yield PS (theory): | 644.6 g | measured: | 607.2 g | (= 94.2 % of theory) |
|---|---|---|---|---|
| Cl-content/batch (theory): | 166.7 g | measured: | 163.9 g | (Amount of Cl in the waste water) |
| Cl-emission/kg PS (theory): | 258.6 g | measured: | 270.0 g | |

The ratio of sulfur to oxygen in the obtained polysulfide was derived from the stoichiometry of the reactants as 1:2,5.

Comparative Example B3: Preparation of a polysulfide using the bis-(2-chlorethyl)-fomral (A3)

The raction of Example B1 was carried out with 393,8 g (2,2 mol) bis-(2-chlorethyl)-formal (A3) instead of the TEG based pre-polymer (I) (A1). The resulting polysulfide had an average molecular weight in the range of 1800-2700 g/mol.

TABLE B3

| yield PS (theory): | 384.6 g | measured: | 360.4 g | (= 93.7 % of theory) |
|---|---|---|---|---|
| Cl-content/batch (theory): | 166.7 g | measured: | 166.2 g | (Amount Cl in the waste water) |
| Cl-emission/kg PS (theory): | 433.4 g | measured: | 461.2 g | |

The ratio of sulfur to oxygen in the obtained polysulfide was derived from the stoichiometry of the ractants as 1:1.

The chloride emissions in the Examples B1 and B2 were 25% and 41% lower, respectively, compared with Comparative Example B3. Thus, the Examples B1 and B2 show an improved salt balance compared to the Comparative Example B3.

The sulfur to oxygen ratio in the Examples B1 and B2 were higher in oxygen content in comparison to Example B3. Thus, the polysulfides prepared accordin to the invention (Examples B1 and B2) are more polar compared to the polysulfide obtained by the Comparative Example B3.

C. Application testing of the polysulfide, produced in accordin gto Examples B1, B2, and Comparative Example B3.

Sealant formulation

Insulating glass sealant formulations were prepared using a conventional laboratory Butterfly mixer. The batch-size in all texts was approx. 1.5 kg.

A number of plasticizers were selected depending on thier polarity relative to the polysulfide (B3). The plasticizers used in the following were: Diethylene Glycol Dibenzoate (DEG) (non-polar (np)) 3,3'-oxydi-1-propanol dibenzoate (DPG) (polar (p)), a blend of DPG/DEG Dibezoate (1:1) (np), Alkyl (C7-C9) Benzyl Phthalate (p), Alkyl (C4) Benzyl Phthalate (p), Di-alkyl (C9) Phthalate (np), Chlorinated paraffin (chlorine content 45-55 wt%) (np).

TABLE 1

Sealant formulation according to the invention: Polymer-Part

| Raw Material | Charging [wt%] | Time [min] | Temperature [° C.] | Remarks |
|---|---|---|---|---|
| Polysulfides prepared according to Examples B1, B2 and Comparative Example B3 | 20.0 | | 20 | Butterfly-Mixer, under temp. and pressure control Charging |
| Plasticizer | 11.7 | | | Charging |
| | | 10 | 25 | intensive mixing at 800/min at 1 bar |
| Omya Omyacarb 2 GU (natural calcium carbonate) | 12.0 | | | Charging |
| | | 5 | 30 | intensive mixing at 800/min at 1 bar |
| | | 10 | | intensive mixing at 800/min at −1 bar |
| Solvay Winnofil SPM (precipitated carlcium carbonate) | 8.3 | | | Charging |
| | | 5 | 45 | intensive mixing at 800/min at 1 bar |
| | | 10 | | intensive mixing at 800/min at −1 bar |
| Omya Omyacarb 6 AL (natural calcium carbonate) | 47.4 | | | Charging |
| | | 5 | 55 | intensive mixing at 800/min at 1 bar |
| | | 10 | | intensive mixing at 800/min at −1 bar |
| Evonik Dynasilan Glymo (organosilane) | 0.6 | | | Charging |
| | | 5 | 65 | intensive mixing at 800/min at 1 bar |
| | | 15 | | intensive mixing at 800/min at −1 bar |
| | | | 65 | Break vacuum and keep the batch for 1d at 25° C. before further testing |

TABLE 2

Sealant formulation according to the invention: Curative-Part

| Raw Material | Charging [wt %] | Time [min] | Temperature [° C.] | Remarks |
|---|---|---|---|---|
| Honeywell MnO$_2$, Type FA | 27.0 | | Max.: 45 | Butterfly-Mixer, under temp. and pressure control Charging |
| Ferro Santicizer 278 (high molecular weight | 27.0 | | Max.: 45 | Charging |

TABLE 2-continued

Sealant formulation according to the invention: Curative-Part

| Raw Material | Charging [wt %] | Time [min] | Temperature [° C.] | Remarks |
|---|---|---|---|---|
| phtalathic plasticizer) | | | | |
| Eastman Benzoflex 9-88 (benzoate based plasticizer) | 27.0 | | Max.: 45 | Charging |
| Water | 0.5 | | | Charging |
| | | 15 | Max.: 45 | intensive mixing at 20/min at 1 bar |
| Cabot Carbon Black, Type 465 | 8.1 | | | Charging |
| | | 15 | Max.: 45 | intensive mixing at 20/min at 1 bar |
| Omya Omyacarb 6 AL (natural calcium carbonate) | 5.5 | | Max.: 45 | Charging |
| Evonik FK 320 (precipitated silica) | 3.2 | | Max.: 45 | Charging |
| | | 15 | Max.: 45 | intensive mixing at 20/min at 1 bar |
| Several suppliers Tetramethy-Thiram-disulfide (TMTD) | 1.3 | | | Charging |
| | | 15 | Max.: 45 | intensive mixing at 20/min at 1 bar |
| Several suppliers N,N'-Diphenylguanidin (DPG) | 0.4 | | | Charging |
| | | 15 | Max.: 45 | intensive mixing at 20/min at 1 bar |
| | | 15 | | intensive mixing at 20/min at −1 bar |
| | | | Max.: 45 | Tripple roll mill, milling to 20 micron particle size. Keep the batch for 1d at 25° C. before further testing |

The application behavior of the polysulfides B1 and B2 and the polysulfide of Comparative Example B3 were tested in an insulating glass sealant prepared according to Table 1 (Polymer-Part) and Table 2 (Curative-Part). Both parts were thoroughly mixed according the mixing ratio 100:9 by weight (Polymer-part: Curative-Part).

Application test

Application properties were determined of the sealants prepared accordin gto Table 1 and Table 2, with regard to Shore A (DIN _B 53505:2000) behavior after 24 hours and after 48 hours, and with regard to the Tensile test (Elongation) after 24 hours (DIN 53455:1981). All sealants contained DPG (p) as the plasticizer and 20 wt% of the polysulfide B1, B2, or B3, respectively. Testing was peformed on the sealants after aging for 1 day at 23° C. and 50% relative humidity (rH). (23° C. and 50% rH are also abbreviated with NL in Table 4).

TABLE 3

Application test (Plasticizer DPG (p))
Results of sealant application testing containing 20 wt % polysulfide prepared according to Examples B1, B2 or Comparative Example B3, respectively

| | Comparative Example B3 Ageing: 1d | Example B2 Ageing: 1d | Example B1 Ageing: 1d |
|---|---|---|---|
| Test conditions (% rel. Humidity (rH)./° C.) | 49/23 | 48/22 | 50/23 |
| Viscosity of A comp. @ 10 s$^{-1}$ (Pas) | 289 | 300 | 278 |
| Viscosity of B comp. @ 10 s$^{-1}$ (Pas) | 30 | 30 | 30 |
| Mixing ratio by weight 100 to | 9 | 9 | 9 |
| Mixing ratio by volume 100 to | 10 | 10 | 10 |
| Pot life (min) | 36 | 40 | 32 |
| Tack free time (min) | 38 | 42 | 35 |
| Shore A Test (DIN 53505) | | | |
| Shore A (after 24 h NL) (5 s) | 44 | 43 | 46 |
| Shore A (after 24 h NL) (3 min) | 40 | 40 | 42 |
| Shore A (after 24 h 60 ° C.) (5 s) | 44 | 47 | 47 |
| Shore A (after 24 h 60 ° C.) (3 min) | 41 | 43 | 44 |
| Shore A (after 48 h 60 ° C.) (5 s) | 47 | 49 | 47 |
| Shore A (after 48 h 60 ° C.) (3 min) | 43 | 46 | 44 |
| Tensile test (Film 2 mm) after 24 h 23°/50% rH (DIN 53455) | | | |
| Modulus @ 10% elongation (N/mm$^2$) | 0.3 | 0.3 | 0.3 |
| Modulus @ 25% elongation (N/mm$^2$) | 0.5 | 0.5 | 0.6 |
| Modulus @ 50% elongation (N/mm$^2$) | 0.9 | 0.9 | 1.0 |
| Modulus @ 100% elongation (N/mm$^2$) | 1.5 | 1.4 | 1.5 |
| Tensile strength (N/mm$^2$) | 1.5 | 1.5 | 1.5 |
| Elongation @ break (%) | 105 | 114 | 97 |
| Tensile test (Film 2 mm) 24 h 23°/50% rH + 24 h 60° C. (DIN 53455) | | | |
| Modulus @ 10% elongation (N/mm$^2$) | 0.3 | 0.3 | 0.3 |
| Modulus @ 25% elongation (N/mm$^2$) | 0.6 | 0.6 | 0.6 |
| Modulus @ 50% elongation (N/mm$^2$) | 1.0 | 1.0 | 1.0 |
| Modulus @ 100% elongation (N/mm$^2$) | 0 | 1.6 | 0 |
| Tensile strength (N/mm$^2$) | 1.4 | 1.6 | 1.5 |

TABLE 3-continued

Application test (Plasticizer DPG (p))
Results of sealant application testing containing 20 wt %
polysulfide prepared according to Examples B1, B2 or
Comparative Example B3, respectively

|  | Comparative Example B3 Ageing: 1d | Example B2 Ageing: 1d | Example B1 Ageing: 1d |
|---|---|---|---|
| Elongation @ break (%) | 83 | 102 | 83 |

As can be seen from Table 3, the sealants containing the polysulfides B1 or B2, obtained by the low-salt process according to the invention, which process has a lower halogen content of the raction mixture compared to the process of Comparative Example B3, shows at least equivalent application preformance, such as Elongation and Shore A hardness of the sealant, compared to the sealant containing the polysulfide of Comparative Example B3.

Compatibility of the sealant containing the polysulfides B1, B2, or B3 with plasticizers.

The compatibility of the sealant prepared accordin to Table 1 and Table 2, containing the polysulfides of Examples B1, B2 or of Comparative Example B3, respectively, with different plasticizers was assessed by visual inspection of the cured sealant matrics comprising the polysulfide and the plasticizer. If no migration of plasticizer out of the matrix was observed, the polysulfide and the plasticizer were compatible. If migration was observed, the polysulfide and the plasticizer were incompatible. In addition, the cohesion or adhesion behavior (referred to in Table 4 as Adhesion behavior) of the sealant to glass substrate was evaluated in accordance to DIN 53504:2009. In this regard, adhesion means: no chemical adhesion; only physical adhesion and cohesion means: chemical adhesion. Cohesive behavior was desired.

TABLE 4

Compatibility of the sealant containing the polysulfides B1, B2, or B3 with the plasticizers

| | Sealant containing the polymer prepared according to | | |
|---|---|---|---|
| Compatibility of sealant formulation to Plasticizer | Example B3 | Example B2 | Example B1 |
| Diethylene Glycol Dibenzoate (DEG) (np) | | | |
| Compatibitity to sealant formulation | Incompatible | Compatible | Compatible |
| Adhesion behaviour to glass substrate (p) 3,3'-oxydi-1-propanol dibenzoate (DPG) (p) | Adhesive | Cohesive | Adhesive / Cohesive |
| Compatibitity to sealant formulation | Compatible | Compatible | Compatible |
| Adhesion behaviour to glass substrate (polar (p)) Blend of DPG/DEG Dibenzoate (1:1) (np) | Cohesive | Cohesive | Cohesive |
| Compatibitity to sealant formulation | Compatible | Compatible | Compatible |
| Adhesion behaviour to glass substrate (p) Alkyl (C7-C9) Benzyl | Adhesive | Cohesive | Cohesive |

TABLE 4-continued

Compatibility of the sealant containing the polysulfides B1, B2, or B3 with the plasticizers

| | Sealant containing the polymer prepared according to | | |
|---|---|---|---|
| Compatibility of sealant formulation to Plasticizer | Example B3 | Example B2 | Example B1 |
| Phthalate (p) | | | |
| Compatibitity to sealant formulation | Compatible | Compatible | Compatible |
| Adhesion behaviour to glass substrate (p) Alkyl (C4) Benzyl Phthalate (p) | Cohesive | Cohesive | Cohesive |
| Compatibitity to sealant formulation | Compatible | Compatible | Compatible |
| Adhesion behaviour to glass substrate (p) Di-alkyl (C9) Phthalate (np) | Adhesive/ Cohesive | Cohesive | Cohesive |
| Compatibitity to sealant formulation | Incompatible | Incompatible | Incompatible |
| Adhesion behaviour to glass substrate (P) Chlorinated paraffins (chlorine content 45-55 wt %) (np) | Adhesive | Adhesive | Adhesive |
| Compatibitity to sealant formulation | Compatible | Compatible | Compatible |
| Adhesion behaviour to glass substrate (P) | Cohesive | Cohesive | Cohesive |

As can be seen from Table 4, the sealants containing the polysulfides B1 or B2, prepared by the low-salt process according to the invention, show comparable compatibility and application properties (cohesion or adhesion behavior) compared to the sealant containing the polysulfide of Comparative Example 3.

Cohesion or Adhesion of the sealant to polar (p) and non-polar (np) surfaces (Plasticizer DPG (p))

The cohesion or adhesion behavior (referred to in Table 5 as Adhesion behavior) of the sealant prepared according to Table 1 and Table 2, containing the polysulfides of Examples B1 or B2 was compared to the sealant containing the polysulfide of Comparative Example B3 with regard to polar (p) and non-polar (np) surfaces. The polarity of a surface was established by determining the contact angle between a water drop and the contact surface (Reference norm is DIN EN 828:2013-04). A hydrophilic or polar surface (p) has a low contact angle (<90°) and a hydrophobic or non-polar surface (np) has a high cantact angle (>90°). The cohesion or adhesion behavior was assessed in accordance with DIN 53504:2009. The sealants contained the plasticizer DPG (p). The sealants were applied to the respective testing surface. The polymeric surfaces (PUR) were additionally cured after the application, prior to testing. Cohesive behavior was desired.

TABLE 5

Sealant Adhesion behavior on different polar (p) and non-polar (np) surfaces

| | Sealant containing the polymer prepared according to | | |
|---|---|---|---|
| | Example B3 | Example B2 | Example B1 |
| Adhesion behaviour on polymeric surfaces [acc. DIN 53504] Polyurethanes (PUR) (OH-terminiated Polybutadiene)-based) (np) | | | |
| Modulus at 25% elonagtion [N/mm²] | 0.4 | 0.6 | 0.5 |
| Tensile strength [N/mm²] | 1.2 | 1.5 | 1.4 |
| Break-Type (Cohesive/Adhesive) | Adhesive/Cohesive | Cohesive | Cohesive |
| Polyurethanes (PUR) (Polyether-based) (np) | | | |
| Modulus at 25% elonagtion [N/mm²] | 0.4 | 0.6 | 0.5 |
| Tensile strength [N/mm²] | 1.5 | 1.6 | 1.5 |
| Break-Type (Cohesive/Adhesive) | Adhesive/Cohesive | Cohesive | Cohesive |
| Polyacrylates (PMMA) (p) | | | |
| Modulus at 25% elonagtion [N/mm²] | 0.6 | 0.9 | 0.8 |
| Tensile strength [N/mm²] | 1.5 | 1.7 | 1.6 |
| Break-Type (Cohesive/Adhesive) | Adhesive/Cohesive | Cohesive | Cohesive |
| Polysulfides (Bis (2-chlorethyl) formal based) (p) | | | |
| Modulus at 25% elonagtion [N/mm²] | 1.1 | 1.3 | 1.2 |
| Tensile strength [N/mm²] | 2.2 | 2.4 | 2.3 |
| Break-Type (Cohesive/Adhesive) | Cohesive | Cohesive | Cohesive |
| Epoxies (EP) (p) | | | |
| Modulus at 25% elonagtion [N/mm²] | 0.8 | 0.9 | 0.8 |
| Tensile strength [N/mm²] | 1.6 | 1.8 | 1.8 |
| Break-Type (Cohesive/Adhesive) | Cohesive | Cohesive | Cohesive |
| Adhesion behaviour to inorganic/metallic surfaces [acc. DIN 53504] Stainless steel (p) | | | |
| Modulus at 25% elonagtion [N/mm²] | 0.9 | 1.1 | 1.1 |
| Tensile strength [N/mm²] | 0.5 | 1.9 | 1.8 |
| Break-Type (Cohesive/Adhesive) | Adhesive/Cohesive | Cohesive | Cohesive |
| Galvanized steel (p) | | | |
| Modulus at 25% elonagtion [N/mm²] | 0.9 | 1.1 | 1.0 |
| Tensile strength [N/mm²] | 1.6 | 1.9 | 1.7 |
| Break-Type (Cohesive/Adhesive) | Cohesive | Cohesive | Cohesive |
| Aluminium (anodized) (p) | | | |
| Modulus at 25% elonagtion [N/mm²] | 0.7 | 1.1 | 1.0 |
| Tensile strength [N/mm²] | 1.4 | 1.9 | 1.7 |
| Break-Type (Cohesive/Adhesive) | Cohesive | Cohesive | Cohesive |
| Glass (p) | | | |
| Modulus at 25% elonagtion [N/mm²] | 0.9 | 1.1 | 0.9 |
| Tensile strength [N/mm²] | 1.9 | 2.0 | 1.9 |
| Break-Type (Cohesive/Adhesive) | Cohesive | Cohesive | Cohesive |

As can be seen from Table 5, the sealants containing polysulfides B1 or B2 show a constant cohesive behavior on a variety of polar surfaces. Even on the non-polar surfaces, the sealants containing polysulfides B1 or B2 according to the invention show cohesive behavior. The sealant containing the polysulfide of Comparative Example B3 in contrast, often shows partially adhesive behavior.

The invention claimed is:

1. Process for the preparation of a polysulfide comprising the step of reacting a bis(2-haloalkyl)formal with either (i) sodium polysulfide or (ii) a combination of sodium hydrosulfide and sulfur, the reaction being performed in the absence of a dihaloalkane and in the presence of a pre-polymer (I) according to structure (I)

$$X-(R^2-O)_n-CH_2-O-(R^1-O)_m-CH_2-(O-R^2)_p-X \quad (I),$$

wherein $R^1$ and $R^2$ can be the same or different and are selected from alkane chains containing 2-10 carbon atoms, X is a halogen atom, and n, m, and p are integers that can be the same or different and have a value in the range 1-6.

2. Process according to claim 1, wherein the bis(2-haloalkyl)formal is bis(2-chloroalkyl)formal.

3. Process according to claim 1 wherein the X is a halogen selected from Cl, Br, and I.

4. Process according to claim 3 wherein the X is Cl.

5. Process according to claim 1, wherein the $R^1$ of the pre-polymer (I) is $-CH_2CH_2-$.

6. Process according to claim 1, wherein the $R^2$ of the pre-polymer (I) is $-CH_2-CH_2-$, $-CH_2-CH_2-CH_2-$, or $-CH_2-CH_2-CH_2-CH_2-$.

7. Process according to claim 1, wherein the product resulting from the reaction of the bis(2-haloalkyl)formal with sodium polysulfide in the presence of the pre-polymer (I) is treated with a reduction agent to obtain a liquid polysulfide.

8. Process according to claim 1, wherein the molar ratio of sodium polysulfide (calculated as $Na_2S_x$) relative to the bis(2-haloalkyl)formal is in the range 0.8-1.4.

9. Process according to claim 1, wherein a mixture comprising bis(2-haloalkyl)formal and the pre-polymer (I) is added to an aqueous solution of sodium hydrosulfide and sulfur.

10. Process according to claim 9, wherein the aqueous solution has a temperature in the range of 60 to 100° C.

11. Process according to claim 1, wherein the weight ratio of the bis(2-haloalkyl)formal to the pre-polymer (I) is in the range of 90:10 to 10:90.

12. Product obtained by the process according to claim 1.

13. A composition comprising a product obtained by the process according to claim 1, said composition selected from sealants, adhesives and coating compositions.

* * * * *